(12) United States Patent
Aho et al.

(10) Patent No.: US 10,653,406 B2
(45) Date of Patent: May 19, 2020

(54) LAPAROSCOPIC RETRACTOR DEVICES

(71) Applicant: Mayo Foundation for Medical Education and Research, Rochester, MN (US)

(72) Inventors: Johnathon M. Aho, Rochester, MN (US); Cornelius A. Thiels, Rochester, MN (US); Kimberly A. Holst, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 901 days.

(21) Appl. No.: 15/074,140

(22) Filed: Mar. 18, 2016

(65) Prior Publication Data

US 2016/0278756 A1 Sep. 29, 2016

Related U.S. Application Data

(60) Provisional application No. 62/138,791, filed on Mar. 26, 2015.

(51) Int. Cl.
*A61B 1/32* (2006.01)
*A61B 17/02* (2006.01)
*A61B 17/00* (2006.01)

(52) U.S. Cl.
CPC .... *A61B 17/0218* (2013.01); *A61B 2017/00477* (2013.01); *A61B 2017/00867* (2013.01); *A61B 2017/00876* (2013.01); *A61B 2017/0225* (2013.01)

(58) Field of Classification Search
CPC combination set(s) only.
See application file for complete search history.

(56) References Cited

U.S. PATENT DOCUMENTS

| 6,755,338 | B2 | 6/2004 | Hahnen et al. | |
| 2008/0249534 | A1* | 10/2008 | Gruber | A61B 1/303 606/119 |
| 2015/0223795 | A1* | 8/2015 | Mariani | A61B 17/0218 600/204 |

OTHER PUBLICATIONS

Holst et al., ETP046 "Laparoscopic Hammock: Improve triangulation while minimizing tissue injury," Surgical Spring Week, SAGES & IPEG 2015, Apr. 15-18, 2015, 2 pages, www.sages2015.org, www.ipeg.org.

\* cited by examiner

*Primary Examiner* — Sameh R Boles
(74) *Attorney, Agent, or Firm* — Fish & Richardson P.C.

(57) ABSTRACT

Some devices for atraumatic retraction of tissue include a transcatheter deployable mesh hammock that is well-suited for laparoscopic, endoscopic, and robotic surgeries. Methods for atraumatic retraction of tissue include wrapping a mesh material around the tissue in a cradle-like fashion. In some embodiments, magnetic coupling of the proximal and distal ends of the mesh material can provide tissue containment and retractor securement to facilitate tissue retraction.

11 Claims, 2 Drawing Sheets

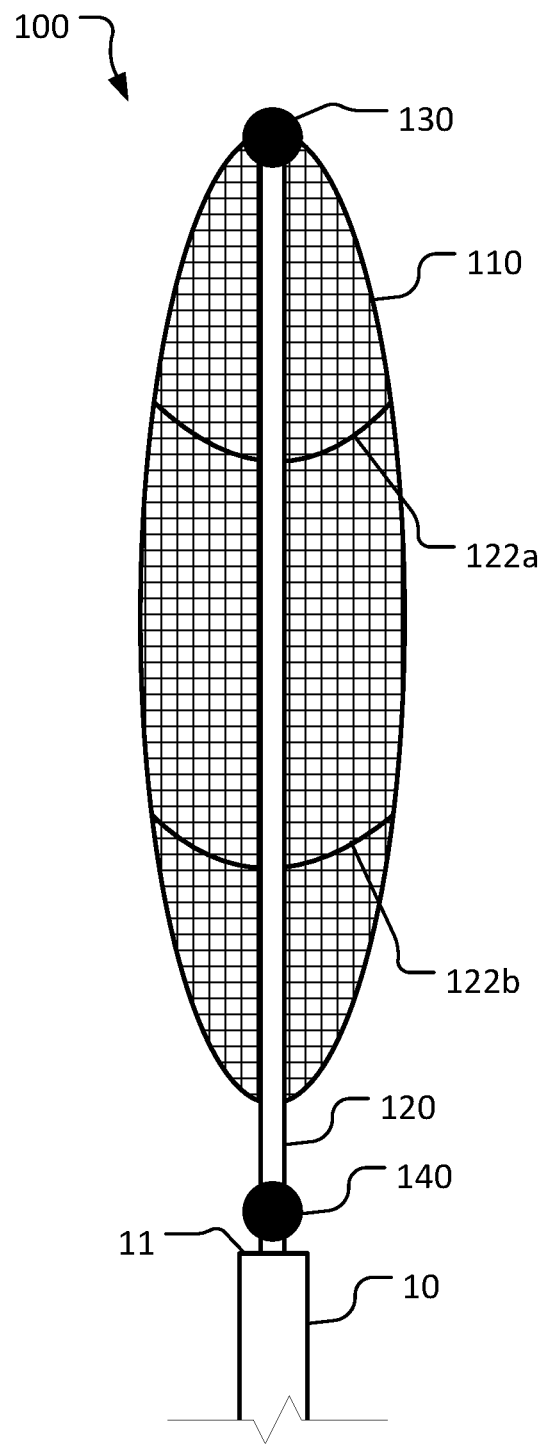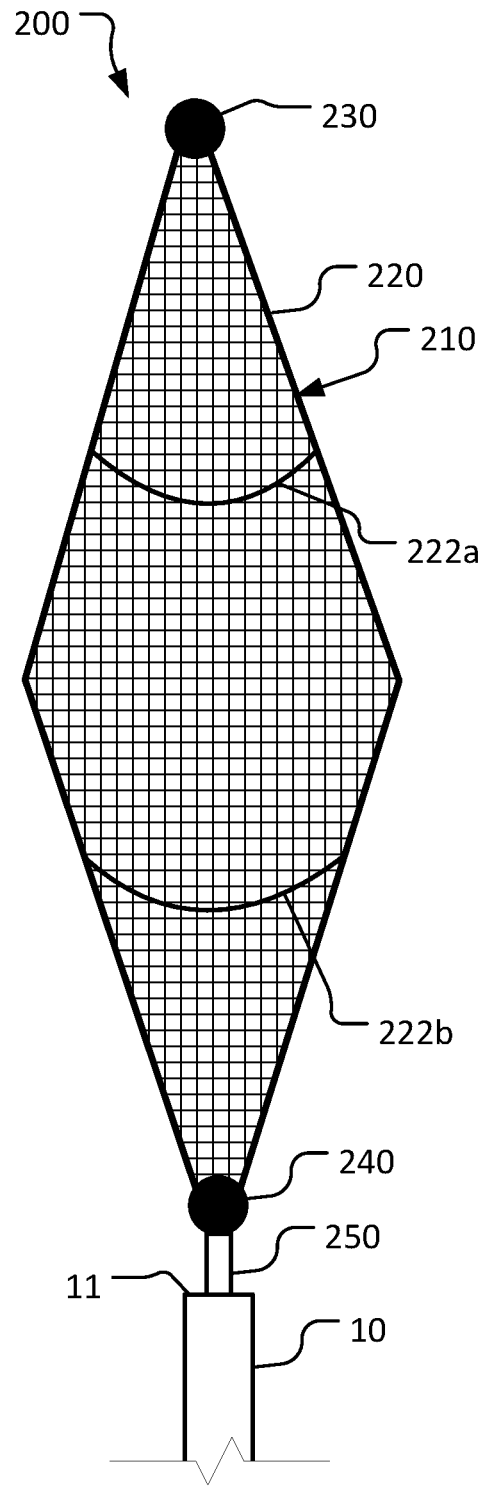
FIG. 1
FIG. 2

LAPAROSCOPIC RETRACTOR DEVICES

CROSS-REFERENCE TO RELATED APPLICATIONS

This application claims the benefit of U.S. Provisional Application Ser. No. 62/138,791, filed Mar. 26, 2015. The disclosure of the prior application is considered part of (and is incorporated by reference in) the disclosure of this application.

BACKGROUND

1. Technical Field

This document relates to devices and methods for retraction of tissue. For example, this document relates to laparoscopic, endoscopic, and robotic surgery devices and methods for atraumatic retraction of tissue by wrapping a mesh material around the tissue in a cradle-like fashion.

2. Background Information

Optimal visualization of the operative field is a fundamental principle in surgery. Any technique that improves intra-operative visualization has the potential to make surgery safer and more cost efficient.

With the advent of minimally invasive surgery, the utilization of laparoscopic, endoscopic, and robotic surgery is becoming the standard of care for many abdominal surgeries. However, there are areas of the abdominal cavity in which the minimally invasive approach is still challenging. For example, small bowel loops frequently obscure the paraaortic surgical field, especially in obese patients.

Retraction of tissue that is inflamed or requires gentle handling is not well-facilitated using current laparoscopic, endoscopic, and robotic surgery retraction instrumentation. Much of the currently available retraction instrumentation focuses on a grasping or crushing type of maneuver to move tissues and mobilize tissue structures.

An alternative approach to laparoscopic, endoscopic, and robotic surgery retraction would be beneficial, as crushing destroys and traumatizes significant amounts of tissues. The crushing can cause ischemia, as well as rupture of both hollow and solid organs. Further, in some scenarios tumors that are being retracted and dissected may rupture, spilling succus as well as tumor cells.

SUMMARY

This document provides devices and methods for retraction of tissue. For example, this document provides laparoscopic, endoscopic, and robotic surgery devices and methods for atraumatic retraction of tissue by wrapping a mesh material around the tissue in a cradle-like fashion.

In one implementation, a tissue retraction apparatus includes a tissue cradling member comprising a thin and flexible material having a distal end portion and a proximal end portion. The tissue cradling member having a longitudinal length and a lateral width. The tissue retraction apparatus also includes an elongate structural element affixed to the distal end portion of the tissue cradling member and affixed to the proximal end portion of the tissue cradling member. The elongate structural element extends along the longitudinal length of the tissue cradling member. The tissue retraction apparatus also includes a distal coupling member affixed to the distal end portion of the tissue cradling member or to the elongate structural element near the distal end portion of the tissue cradling member. The tissue retraction apparatus also includes a proximal coupling member affixed to the proximal end portion of the tissue cradling member or to the elongate structural element near the proximal end portion of the tissue cradling member. The distal coupling member and the proximal coupling member are selectively coupleable to each other. The retraction apparatus is reconfigurable between a low profile delivery configuration and an expanded deployed configuration. The retraction apparatus is configured to be contained within a delivery sheath when the retraction apparatus is in the low profile delivery configuration.

Such a tissue retraction apparatus may optionally include one or more of the following features. The elongate structural element may be biased to have a nonlinear shape. One or both of the distal coupling member and the proximal coupling member may be a magnet. One or both of the distal coupling member and the proximal coupling member may be an electromagnet. The tissue retraction apparatus may further comprise one or more lateral rib members that are affixed to the elongate structural element and that extend laterally from the elongate structural element. The tissue cradling member may comprise a mesh material. The tissue cradling member may comprise a film material. The elongate structural element may comprise nitinol. The longitudinal length of the tissue cradling member may be greater than the lateral width.

In another implementation, a tissue retraction apparatus includes a tissue cradling member comprising a thin and flexible material having a distal end portion and a proximal end portion. The tissue cradling member having a longitudinal length and a lateral width. The tissue retraction apparatus also includes a structural framework element affixed around a general periphery of the tissue cradling member. The tissue retraction apparatus also includes a distal coupling member affixed to the distal end portion of the tissue cradling member or to the structural framework element near the distal end portion of the tissue cradling member. The tissue retraction apparatus also includes a proximal coupling member affixed to the proximal end portion of the tissue cradling member or to the structural framework element near the proximal end portion of the tissue cradling member. The distal coupling member and the proximal coupling member are selectively coupleable to each other. The retraction apparatus is reconfigurable between a low profile delivery configuration and an expanded deployed configuration. The retraction apparatus is configured to be contained within a delivery sheath when the retraction apparatus is in the low profile delivery configuration.

Such a tissue retraction apparatus may include one or more of the following features. The structural framework element may be biased to have a nonlinear shape. One or both of the distal coupling member and the proximal coupling member may be a magnet. One or both of the distal coupling member and the proximal coupling member may be an electromagnet. The tissue retraction apparatus may further comprise one or more lateral rib members that are affixed to the structural framework element and that extend laterally across the tissue cradling member. The tissue member may comprise a mesh material. The tissue cradling member may comprise a film material. The structural framework element may comprise nitinol. The longitudinal length of the tissue cradling member may be greater than the lateral width.

In another implementation, a method of using a tissue retraction apparatus includes advancing a delivery sheath within a body cavity of a patient. The delivery sheath contains a tissue retraction apparatus configured in a low profile delivery configuration. The method also includes expressing the tissue retraction apparatus from the delivery sheath, wherein when the tissue retraction apparatus is expressed from the delivery sheath the tissue retraction apparatus reconfigures to an expanded deployed configuration. The method also includes wrapping the tissue retraction apparatus around a target tissue; coupling the distal coupling member and the proximal coupling member to each other; and applying a retraction force to the target tissue via the tissue cradling member while the distal coupling member and the proximal coupling member are coupled to each other. The tissue retraction apparatus comprises: a tissue cradling member comprising a thin and flexible material having a distal end portion and a proximal end portion; an elongate structural element affixed to the distal end portion of the tissue cradling member and affixed to the proximal end portion of the tissue cradling member, the elongate structural element extending along the longitudinal length of the tissue cradling member; a distal coupling member affixed to the distal end portion of the tissue cradling member or to the elongate structural element near the distal end portion of the tissue cradling member; and a proximal coupling member affixed to the proximal end portion of the tissue cradling member or to the elongate structural element near the proximal end portion of the tissue cradling member. The distal coupling member and the proximal coupling member are selectively coupleable to each other.

As used herein, the term "laparoscopic" should be interpreted to include at least laparoscopic, endoscopic, and robotic surgical techniques.

Particular embodiments of the subject matter described in this document can be implemented to realize one or more of the following advantages. First, in some embodiments the laparoscopic retractor devices provided herein are readily adjustable in size from a low profile delivery configuration to a substantially wider expanded configuration for performing atraumatic retraction of tissue and organs.

Second, the laparoscopic retractor devices provided herein have intuitive and easy to operate designs. Further, the laparoscopic retractor devices provided herein do not include separable pieces or multiple movable parts. In some embodiments, the laparoscopic retractor devices provided herein are designed to minimize the risk of pinching or impinging tissue during the adjustment of the retractors between the contracted and expanded configurations. Advantageously, clinicians can operate the retractor devices without a risk of pieces becoming detached within a body cavity.

Third, the laparoscopic retractor devices provided herein provide atraumatic laparoscopic retraction of tissue by wrapping a mesh material around the tissue in a gentle cradle-like fashion. In that manner, the potential of causing tissue damage such as ischemia, tears, ruptures, and the like, is at least partially mitigated.

Fourth, various surgeries can be performed in a minimally invasive fashion using the devices and methods provided herein. Minimally invasive intra-operative visualization is improved using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 1 is a plan view of an example laparoscopic retraction device in accordance with some embodiments provided herein.

FIG. 2 is a plan view of another example laparoscopic retraction device in accordance with some embodiments provided herein.

Like reference numbers represent corresponding parts throughout.

DETAILED DESCRIPTION

Figure 3:
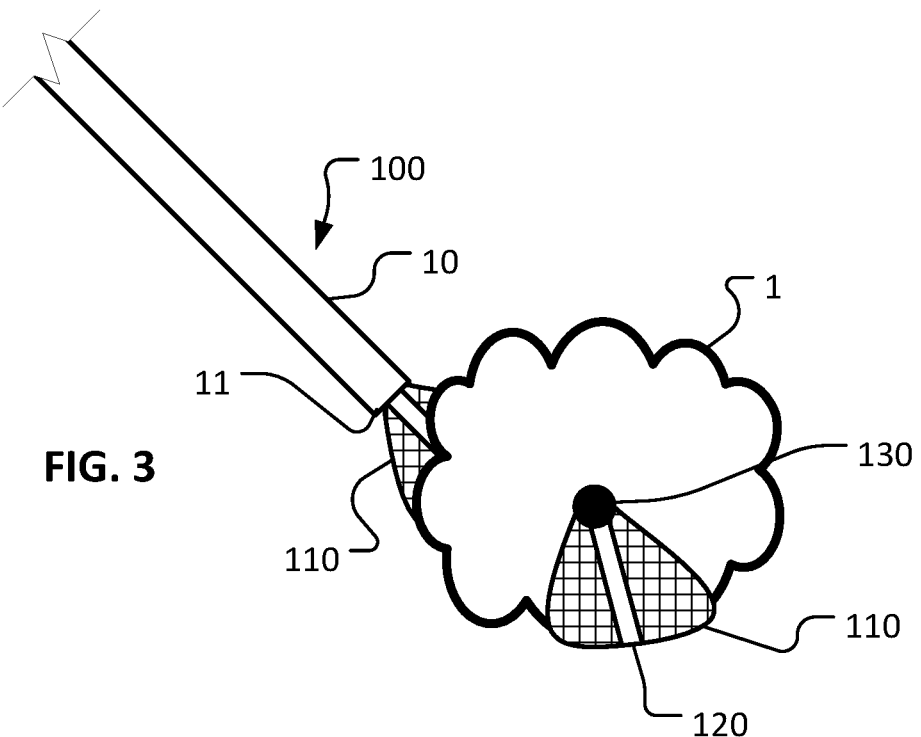
FIG. 3 shows a step of an example method for tissue retraction using an example laparoscopic retraction device in accordance with some embodiments provided herein.

This document provides devices and methods for laparoscopic retraction of tissue. For example, this document provides devices and methods for atraumatic laparoscopic retraction of tissue by wrapping a mesh material around the tissue in a cradle-like fashion.

Many currently available laparoscopic retractors utilize a grasping or crushing modality to move tissues and mobilize tissue structures. One alternative to laparoscopic retraction using a traumatic crushing process are apparatuses that use a material to "hug" or "wrap" around the structure being manipulated. An analog of such atraumatic methods of retraction and tissue manipulation is used in some open procedures, as there is significantly more access to the body cavity being operated upon. The difficulty in using this method for laparoscopic surgery is in the limited access granted by laparoscopic port sites to allow either a hand or an instrument that is large enough to "wrap" the object.

This disclosure describes devices such as a deployable "hammock" that may be used to wrap tissue objects laproscopically. Some such devices have a hammock-like webbing that is deployable and able to grab the object posteriorly, to thereby gently provide retraction to delicate structures.

In some embodiments, a device for fixation attaches back to the instrument after wrapping around the tissue object. In some embodiments, such a fixation device utilizes proximal and distal magnets to provide convenient fixation and closure of the "hammock" portion back to the instrument. In some embodiments, when the proximal magnet is pulled back into the instrument, the hammock portion is disengaged and the mesh portion is able to be retracted back into the instrument. These devices will be of significant utility as many current crushing-type retraction instruments do not provide appropriate tactile feedback to allow the surgeon to be able to judge truly how much force is being applied to various structures being manipulated.

The laparoscopic retractor devices provided herein can be used for performing surgeries by helping to gain exposure and visualization of the surgical field in the body, such as in areas of the abdomen that are obscured by the bowel and other tissues and structures. In addition to such intra-abdominal surgeries, in some cases the laparoscopic retractor devices provided herein may be used for procedures in other medical specialties such as, but not limited to, urology, vascular surgery, thoracic surgery, and general surgery. It should be understood that the devices provided herein have utility for uses such as, but not limited to, laparoscopic, endoscopic, and robotic surgeries.

Referring to FIG. 1, an example laparoscopic retractor 100 can be used to gently provide retraction to tissue structures. In the depicted non-limiting embodiment, laparoscopic retractor 100 includes a tissue cradle member 110, a structural spine element 120, a distal coupling member 130, and a proximal coupling member 140.

Laparoscopic retractor 100 can be deployed in a patient's body using a delivery sheath 10. In some implementations, delivery sheath 10 is slidably disposed within a channel (lumen) of a laparoscopic instrument or laparoscope. Accordingly, in some implementations laparoscopic retractor 110 can be deployed within a patient's body in a minimally invasive manner.

Laparoscopic retractor 100 is reconfigurable between a low profile delivery configuration and an expanded deployed configuration. FIG. 1 shows laparoscopic retractor 100 in its fully expanded deployed configuration. When laparoscopic retractor 100 is in its low profile delivery configuration, laparoscopic retractor 100 is contained within a lumen of delivery sheath 10. It should be understood that in the context of this disclosure, "deployed configuration" means that laparoscopic retractor 100 is not contained within delivery sheath 10. Accordingly, in its deployed configuration, laparoscopic retractor 100 is not constrained by delivery sheath 10. Therefore, laparoscopic retractor 100 is free to expand to a larger diametrical size as laparoscopic retractor 100 reconfigures from its low profile delivery configuration to its deployed configuration. In particular, tissue cradle member 110 will tend to expand as laparoscopic retractor 100 emerges from confinement within delivery sheath 10. While FIG. 1 shows laparoscopic retractor 100 in its fully expanded configuration, it should be understood that in actual use within a patient's body laparoscopic retractor 100 may not expand to exactly the configuration shown. That is the case because, for example, the body cavity space in which laparoscopic retractor 100 is deployed may restrict laparoscopic retractor 100 from fully expanding to the configuration shown.

In some embodiments, tissue cradle member 110 is a thin flexible material. Various types of materials and types of constructions can be used for tissue cradle member 110. For example, in some embodiments tissue cradle member 110 is a mesh material. The mesh material can also be a netting, latticework, webbing, woven material, a knit, and the like. In some such embodiments, tissue cradle member 110 is made of DACRON®, ePTFE, a copolymer, a polyester, a silicone, a urethane, a polyethylene terephthalate, or another biocompatible polymer, or combinations thereof. In some embodiments, tissue cradle member 110 is a film that may or may not be porous. In some embodiments, tissue cradle member 110 is woven of metallic fibers. For example, in some embodiments tissue cradle member 110 is woven of nitinol fibers.

In the depicted embodiment, tissue cradle member 110 is generally ovular in overall shape. It should be understood that the generally ovular shape is not a requirement for all embodiments. For example, in some embodiments tissue cradle member 110 may have other shapes such as, but not limited to, triangular, rectangular, circular, polygonal, reniform, parallelogram, and the like. Tissue cradle member 110 may be symmetrical or nonsymmetrical. In some embodiments, tissue cradle member 110 may be trimmed to a custom shape. In some embodiments, tissue cradle member 110 is a single unitary piece of material. In some embodiments, tissue cradle member 110 comprises two or more pieces of material that either may be attached to each other or may be separated from each other.

Tissue cradle member 110 may have various dimensional proportions (i.e., lengths and widths). For example, in some embodiments tissue cradle member 110 may be about 2 in$^2$ (about 5 cm$^2$). Such embodiments may be, for example, about 1 inch (2.5 cm) wide by about 2 inches (about 5.1 cm) long, but any length and width combination may be used (and non-rectangular shapes may be used). In some embodiments, tissue cradle member 110 may be about 100 in$^2$ (about 645 cm$^2$). It should be understood that, without limitation, tissue cradle member 110 may be any size and all such sizes are within the scope of this disclosure.

In some embodiments, tissue cradle member 110 is attached at two or more locations along the longitudinal length of structural spine element 120. For example, in some embodiments at least a distal portion of tissue cradle member 110 and a proximal portion of tissue cradle member 110 are attached to structural spine element 120. In some embodiments, tissue cradle member 110 is attached to structural spine element 120 at more than two locations along the longitudinal length of structural spine element 120. In some embodiments, stitching, lashing, banding, and/or clips, and the like can be used to attach tissue cradle member 110 to structural spine element 120. In some embodiments, portions of tissue cradle member 110 are disposed on a first side and on an opposite second side of structural spine element 120. In some embodiments, portions of tissue cradle member 110 are adhered to portions of structural spine element 120. In some embodiments, a combination of techniques (including the use of adhesives) are used to attach tissue cradle member 110 to structural spine element 120. Such features and techniques can also be incorporated with other embodiments of laparoscopic retractors provided herein.

In some embodiments, structural spine element 120 is used to push/pull laparoscopic retractor 100 in relation to delivery sheath 10. In the context of this disclosure, when laparoscopic retractor 100 is pushed in relation to delivery sheath 10, it is also referred to as moving laparoscopic retractor 100 distally. Similarly, in the context of this disclosure, when laparoscopic retractor 100 is pulled in relation to delivery sheath 10, it is also referred to as moving laparoscopic retractor 100 proximally. Accordingly, structural spine element 120 can be manipulated by a clinician operator (e.g., surgeon) to move laparoscopic retractor 100 distally and proximally in relation to delivery sheath 10. As described further below, it should also be understood that by manipulation of delivery sheath 10 a clinician can control the positioning of laparoscopic retractor 100 in relation to the patient's anatomy. In some implementations, a clinician may perform multiple actions concurrently. For example, the clinician may extend laparoscopic retractor 100 distally while manipulating the position of distal tip 11 of delivery sheath 10 in relation to the patient's anatomy. In that manner a clinician can, for example, loop tissue cradle member 110 around an organ or portion of tissue in a net, cradle, or hammock-like arrangement.

Structural spine element 120 may be constructed of various types of materials and using various methods of construction. In some embodiments, nitinol (NiTi) is used as the material of structural spine element 120, but other materials such as stainless steel, L605 steel, polymers, MP35N steel, stainless steel alloys, polymeric materials, Pyhnox, Elgiloy, or any other appropriate biocompatible material, and alloys and combinations thereof can be used as the material of structural spine element 120. The superelastic properties of NiTi make it a particularly good candidate material for structural spine element 120 because, for example, NiTi can be shape-set into a desired shape. That is, NiTi can be shape-set so that structural spine element 120 tends to self-conform into a desired shape when structural spine element 120 is unconstrained, such as when structural spine element 120 is deployed out from the delivery sheath 10. When structural spine element 120 is made of NiTi, for example, it may have a spring nature that allows structural spine element 120 to be elastically collapsed or "crushed" to the low-profile delivery configuration for loading and slidably translating in the delivery sheath 10, and then to reconfigure to the expanded configuration as shown in FIG. 1 upon emergence from the delivery sheath 10. Structural spine element 120 may be generally conformable, fatigue resistant, and elastic such that structural spine element 120 can conform to the topography of the tissue to be retracted when laparoscopic retractor 100 is deployed in a patient.

In some embodiments, structural spine element 120 has a column strength that is at least sufficient to facilitate a clinician's control of proximal and distal motions of laparoscopic retractor 100 in relation to delivery sheath 10. In some embodiments, structural spine element 120 is laterally flexible so that a clinician can, for example, loop tissue cradle member 110 around an organ or portion of tissue in a net, cradle, or hammock-like arrangement. In particular embodiments, structural spine element 120 is shape-set with a bias to seek a naturally nonlinear (e.g., curved or angled) shape when structural spine element 120 is unconstrained.

In the depicted embodiment, a first lateral rib member 122a and a second lateral rib member 122b are coupled to structural spine element 120. In some embodiments, more than two such lateral rib members are included. For example, in some embodiments three, four, five, six, seven, eight, nine, ten, or more than ten lateral rib members are included. In some embodiments, no such lateral rib members are included.

First and second lateral rib members 122a and 122b serve to laterally expand tissue cradle member 110, to thereby increase the exposed surface area of tissue cradle member 110. Accordingly, less pressure is exerted by tissue cradle member 110 on tissue when the tissue is retracted using laparoscopic retractor 100. In that manner a clinician can loop tissue cradle member 110 around an organ or portion of tissue in a net, cradle, or hammock-like arrangement to facilitate gentle tissue retraction.

First and second lateral rib members 122a and 122b can be constructed of the same types of materials as described above in reference to structural spine element 120. In some embodiments, first and second lateral rib members 122a and 122b are constructed of the same material as structural spine element 120. In some embodiments, first and second lateral rib members 122a and 122b are constructed of a different material than structural spine element 120. First and second lateral rib members 122a and 122b may have a spring nature that allows first and second lateral rib members 122a and 122b to be elastically collapsed or "crushed" to the low-profile delivery configuration for loading and slidably translating in the delivery sheath 10, and then to self-reconfigure to the expanded configuration as shown in FIG. 1 upon emergence from the delivery sheath 10.

Laparoscopic retractor 100 also includes distal coupling member 130 and proximal coupling member 140. Distal coupling member 130 and proximal coupling member 140 are selectively coupleable to each other. That is, a clinician operator of laparoscopic retractor 100 can initiate coupling between distal coupling member 130 and proximal coupling member 140, as well as initiate decoupling between distal coupling member 130 and proximal coupling member 140.

In the depicted embodiment, distal coupling member 130 and proximal coupling member 140 are each affixed to structural spine element 120. Alternatively, one or both of distal coupling member 130 and proximal coupling member 140 can be affixed to other portions of laparoscopic retractor 100. For example, in some embodiments one or both of distal coupling member 130 and proximal coupling member 140 can be affixed to tissue cradle member 110. In some embodiments, proximal coupling member 140 is affixed to delivery sheath 10 (e.g., near distal tip 11). In such an arrangement, distal coupling member 130 and proximal coupling member 140 could stay engaged while not having tissue cradle member 110 fully out of delivery sheath 10 (e.g., to improve tissue manipulation with minimizing space the device takes up in the body cavity).

Distal coupling member 130 and proximal coupling member 140 can take various forms, i.e., distal coupling member 130 and proximal coupling member 140 can be a variety of different types of mechanisms. In some embodiments, distal coupling member 130 and proximal coupling member 140 are a mechanical ring and hook or prong. For example, distal coupling member 130 can be a ring and proximal coupling member 140 can be a hook or prong that the clinician can positionally manipulate to become engaged with the ring. In some embodiments, such a hook can be selectively deployed or retracted.

In some embodiments, one or both of distal coupling member 130 and proximal coupling member 140 are magnets or magnetic elements. In some embodiments, one or both of distal coupling member 130 and proximal coupling member 140 are neodymium magnets. In some embodiments, one or both of distal coupling member 130 and proximal coupling member 140 are electro-magnets. In some embodiments, one of distal coupling member 130 or proximal coupling member 140 is a magnet while the other of distal coupling member 130 or proximal coupling member 140 is magnetize-able (e.g., a ferromagnetic material).

Other types of distal coupling members 130 and proximal coupling members 140 are also envisioned. For example, one or both of distal coupling member 130 and proximal coupling member 140 can be elements such as, but not limited to, suction cups, latches, spring clips, expandable elements, grasping devices, and the like. In some embodiments, one or both of distal coupling member 130 and proximal coupling member 140 are controllable by a clinician exterior to the patient. For example, in some embodiments the clinician can actuate (e.g., activate and/or deactivate) one or both of distal coupling member 130 and proximal coupling member 140 remotely (e.g., at a controller exterior to the patient). In one such example, distal coupling member 130 is magnetic and proximal coupling member 140 is an electromagnet that can be activated and deactivated by the clinician.

In some embodiments, both distal coupling member 130 and proximal coupling member 140 are magnets. In some such embodiments, distal coupling member 130 and proximal coupling member 140 can be coupled and/or decoupled by physically adjusting the alignment of the respective magnets' polarities. The physical adjustment can result from relative rotation and/or translation between distal coupling member 130 and proximal coupling member 140. For example, having the distal coupling member 130 fixed and proximal coupling member 140 rotatable can provide selective coupling and decoupling of distal coupling member 130 and proximal coupling member 140.

Referring to FIG. 2, another example laparoscopic retractor 200 can be used to gently provide retraction to tissue structures. In the depicted non-limiting embodiment, laparoscopic retractor 200 includes a tissue cradle member 210, a structural framework element 220, a distal coupling member 230, a proximal coupling member 240, and a control shaft 250.

Structural framework element 220 is affixed to control shaft 250. In some implementations, a clinician can control laparoscopic retractor 200 by manipulation of: (i) control shaft 250, (ii) delivery sheath 10, and (iii) one or more activation means for distal coupling member 230 and/or proximal coupling member 240. In some embodiments, no such activation means for distal coupling member 230 and/or proximal coupling member 240 is included.

Laparoscopic retractor 200 can be constructed analogously to laparoscopic retractor 100 (and to any or all variations thereof) except that laparoscopic retractor 200 includes rigid structural framework element 220 around the periphery of tissue cradle member 210. In some embodiments, no central structural member (e.g., like structural spine element 120 as shown in FIG. 1) is included in laparoscopic retractor 200. In some embodiments, both rigid structural framework element 220 and a central structural member are included.

It should be understood that multiple laparoscopic retractor device embodiments are described herein. It should also be understood that one or more of the features described in the context of a particular device may be combined with one or more features of any other device or multiple devices described herein. That is, the features of the laparoscopic retractors described herein may be mixed and matched to provide hybrid laparoscopic retractor device embodiments, and such hybrid laparoscopic retractor device embodiments are within the scope of this disclosure. In some examples, one or more features described with respect to a particular device may replace or be substituted for one or more features of another device. In some examples, one or more features described with respect to a particular device may be added to or included with another device. Also, various combinations or sub-combinations of any of the features described herein may generally be used with any of the devices described herein. It should be understood that the laparoscopic retractor devices provided herein are scalable to a broad range of sizes and proportions so that the laparoscopic retractor devices can be used in a variety of different anatomies, target tissues, and types of implementations.

Figure 4:
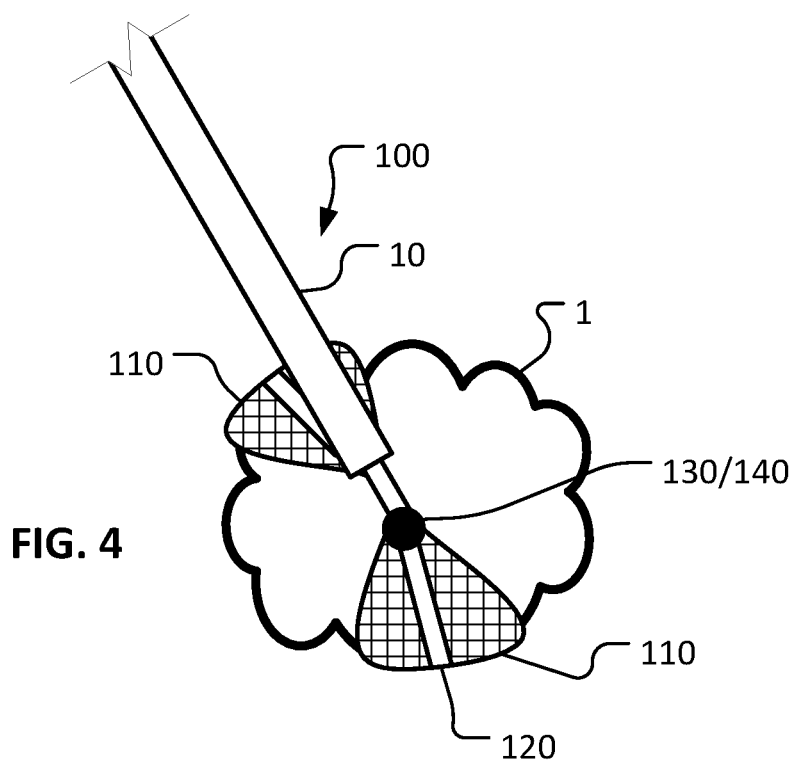
FIG. 4 shows another step of the example method for tissue retraction using an example laparoscopic retraction device in accordance with some embodiments provided herein.

Referring to FIGS. 3 and 4, an example technique for using laparoscopic retractor 100 to retract an example tissue 1 is illustrated. FIG. 3 shows the orientation of laparoscopic retractor 100 in relation to tissue 1 as tissue cradle member 110 is partially wrapped around tissue 1. FIG. 4 shows the orientation of laparoscopic retractor 100 in relation to tissue 1 as tissue cradle member 110 is fully wrapped around tissue 1, and as distal coupling member 130 and proximal coupling member 140 are coupled together. In that arrangement, laparoscopic retractor 100 can lift, slide, or otherwise retract tissue 1. Thereafter, distal coupling member 130 and proximal coupling member 140 can be decoupled, tissue cradle member 110 can be retracted into delivery sheath 10, and the delivery sheath 10 containing laparoscopic retractor 100 can be removed from the patient's body.

In some implementations, tissue cradle member 110 is wrapped around tissue 1 by the clinician's manipulation of distal tip 11 of delivery sheath 10 around the tissue 1 as tissue cradle member 110 is being expressed from sheath 10. In some embodiments, structural spine element 120 (or other structural elements supporting tissue cradle member 110, e.g., structural framework element 220 of FIG. 2) has a shape-memory that biases tissue cradle member 110 to extend laterally from distal tip 11 of delivery sheath 10 as laparoscopic retractor 100 is being expressed from delivery sheath. Such a lateral bias can assist with placing tissue cradle member 110 around tissue 1.

Retraction forces from laparoscopic retractor 100 can be applied on tissue 1 while tissue cradle member 110 is partially wrapped around tissue 1. That is, some extent of retraction can be performed without creating a complete cradle by tissue cradle member 110 around tissue 1.

When tissue cradle member 110 is fully wrapped around tissue 1, distal coupling member 130 and proximal coupling member 140 can become coupled so that laparoscopic retractor 100 can apply substantial retraction forces to tissue 1. In some embodiments, a clinician operator of laparoscopic retractor 100 can initiate coupling between distal coupling member 130 and proximal coupling member 140, as well as initiate decoupling between distal coupling member 130 and proximal coupling member 140. In some embodiments, coupling between distal coupling member 130 and proximal coupling member 140 can occur automatically, and decoupling of distal coupling member 130 and proximal coupling member 140 can be initiated by the clinician operator.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A tissue retraction apparatus comprising:
   a tissue cradling member comprising a thin and flexible material having a distal end portion and a proximal end portion, the tissue cradling member defining a longitudinal length and a lateral width;
   an elongate structural element affixed to the distal end portion of the tissue cradling member and affixed to the proximal end portion of the tissue cradling member, the elongate structural element extending along the longitudinal length of the tissue cradling member;
   a distal coupling member affixed to the distal end portion of the tissue cradling member or to the elongate structural element near the distal end portion of the tissue cradling member; and
   a proximal coupling member affixed to the proximal end portion of the tissue cradling member or to the elongate structural element near the proximal end portion of the tissue cradling member,
   wherein the distal coupling member and the proximal coupling member are selectively coupleable to each other after wrapping the tissue cradling member around tissue in a cradle-like fashion,
   wherein the retraction apparatus is reconfigurable between a low profile delivery configuration and an expanded deployed configuration, and wherein the retraction apparatus is configured to be contained within a delivery sheath when the retraction apparatus is in the low profile delivery configuration.

2. The tissue retraction apparatus of claim 1, wherein the elongate structural element is biased to have a nonlinear shape.

3. The tissue retraction apparatus of claim 1, wherein one or both of the distal coupling member and the proximal coupling member is a magnet.

4. The tissue retraction apparatus of claim 3, wherein one or both of the distal coupling member and the proximal coupling member is an electromagnet.

5. The tissue retraction apparatus of claim 1, further comprising one or more lateral rib members that are affixed to the elongate structural element and that extend laterally from the elongate structural element.

6. The tissue retraction apparatus of claim 1, wherein the tissue cradling member comprises a mesh material.

7. The tissue retraction apparatus of claim 1, wherein the tissue cradling member comprises a film material.

8. The tissue retraction apparatus of claim 1, wherein the elongate structural element comprises nitinol.

9. The tissue retraction apparatus of claim 1, wherein the longitudinal length is greater than the lateral width.

10. The tissue retraction apparatus of claim 1, wherein the distal coupling member and the proximal coupling member comprise a ring and a hook.

11. The tissue retraction apparatus of claim 10, wherein the hook is selectively deployable.

* * * * *